US011118746B1

(12) United States Patent
Cao

(10) Patent No.: US 11,118,746 B1
(45) Date of Patent: Sep. 14, 2021

(54) ELECTRONIC CANDLE

(71) Applicant: Liling Cao, Shenzhen (CN)

(72) Inventor: Liling Cao, Shenzhen (CN)

( * ) Notice: Subject to any disclaimer, the term of this patent is extended or adjusted under 35 U.S.C. 154(b) by 0 days.

(21) Appl. No.: 17/131,611

(22) Filed: Dec. 22, 2020

(30) Foreign Application Priority Data

Nov. 4, 2020 (CN) ......................... 202011219400.3

(51) Int. Cl.
*F21S 10/04* (2006.01)
*F21S 6/00* (2006.01)
*F21V 23/00* (2015.01)
*A61L 9/12* (2006.01)
*F21V 15/01* (2006.01)

(52) U.S. Cl.
CPC ............... *F21S 10/046* (2013.01); *A61L 9/12* (2013.01); *F21S 6/001* (2013.01); *F21V 15/01* (2013.01); *F21V 23/003* (2013.01); *A61L 2209/11* (2013.01); *A61L 2209/12* (2013.01)

(58) Field of Classification Search
CPC ........ F21S 10/04; F21S 10/043; F21S 10/046; F21S 6/001; F21V 15/01; F21V 23/003; A61L 9/12; A61L 2209/11; A61L 2209/12
See application file for complete search history.

(56) References Cited

U.S. PATENT DOCUMENTS

| | | | | |
|---|---|---|---|---|
| 10,010,640 | B1 * | 7/2018 | Li | A61L 9/032 |
| 10,184,628 | B2 * | 1/2019 | Lin | F21S 10/043 |
| 10,436,396 | B2 * | 10/2019 | Cao | F21S 6/001 |
| 2006/0120080 | A1 * | 6/2006 | Sipinski | A61L 9/127 362/253 |
| 2007/0292812 | A1 * | 12/2007 | Furner | F23D 3/24 431/289 |
| 2019/0338901 | A1 * | 11/2019 | Ray | F21S 6/001 |
| 2020/0114038 | A1 | 4/2020 | Yuan | |
| 2020/0116321 | A1 | 4/2020 | Li | |

FOREIGN PATENT DOCUMENTS

| | | | |
|---|---|---|---|
| CN | 110500552 | A | 11/2019 |
| GB | 2564783 | B | 7/2019 |

* cited by examiner

*Primary Examiner* — Alan B Cariaso
(74) *Attorney, Agent, or Firm* — Hemisphere Law, PLLC; Zhigang Ma

(57) ABSTRACT

An electronic candle includes a housing, an electric wire extending from the upper end of the housing, a flame piece connected to the tail end of the electric wire and a control circuit arranged in the housing and electrically connected with the electric wire. At least the middle part of the upper end of the housing is formed into a concave portion, a hole is formed in the concave portion, a container for containing liquid is arranged below the hole, the opening of the container is hermetically connected with the upper end of the housing, and the hole is communicated with the inside of the container. Liquid can be contained in the concave portion to simulate molten wax water formed at the upper end of a candle body after a real candle is ignited, and the simulation degree is higher. The liquid can be a liquid containing fragrance.

10 Claims, 2 Drawing Sheets

ELECTRONIC CANDLE

CROSS-REFERENCE TO RELATED APPLICATION

This application claims priority benefit of Chinese Application 202011235326.4, filed on Nov. 9, 2020, said application being fully incorporated by reference herein.

BACKGROUND OF THE INVENTION

1. Technical Field

The present invention relates to electronic candles.

2. Description of Related Art

Electronic candles are widely favored by consumers because of their environmental protection and energy conservation. Now there are electronic candles with an aromatherapy function, either through an atomizer that atomizes an aromatic liquid and sprays it out, or by adding an aromatic liquid or solid to make the aroma volatilize. The first type of aromatherapy candle has poor candle simulation effect, complex structure, and large consumption of aromatherapy raw materials is required. The second type of aromatherapy candle needs to be heated, generally by heat generated by the circuit board itself, and the effect is not good.

BRIEF DESCRIPTION OF THE SEVERAL VIEWS OF THE DRAWINGS

The foregoing and other exemplary purposes, aspects and advantages of the present invention will be better understood in principle from the following detailed description of one or more exemplary embodiments of the invention with reference to the drawings, in which.

DETAILED DESCRIPTION OF THE INVENTION

The invention will now be described in detail through several embodiments with reference to the accompanying drawings.

Figure 1:
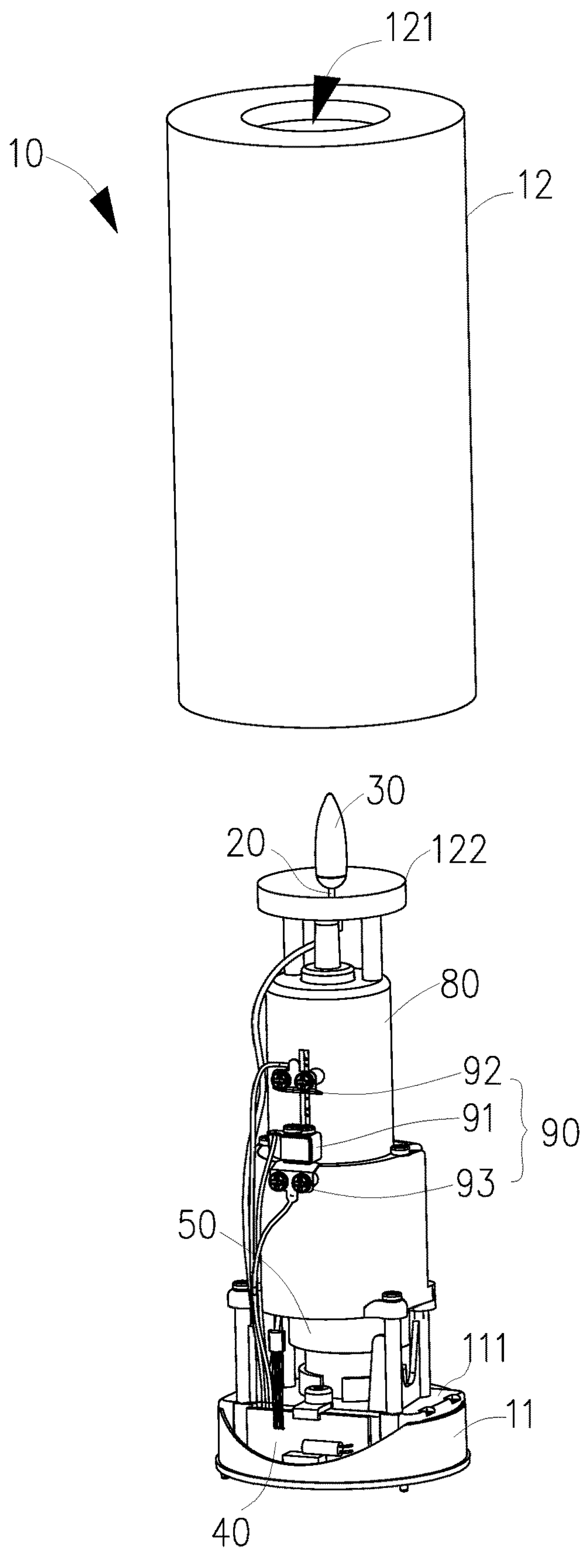
FIG. 1 is an exploded view of an electronic candle according to an embodiment of the present invention.
Figure 2:
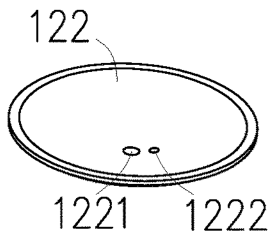
FIG. 2 is a schematic view of a tray of the electronic candle in FIG. 1.
Figure 3:
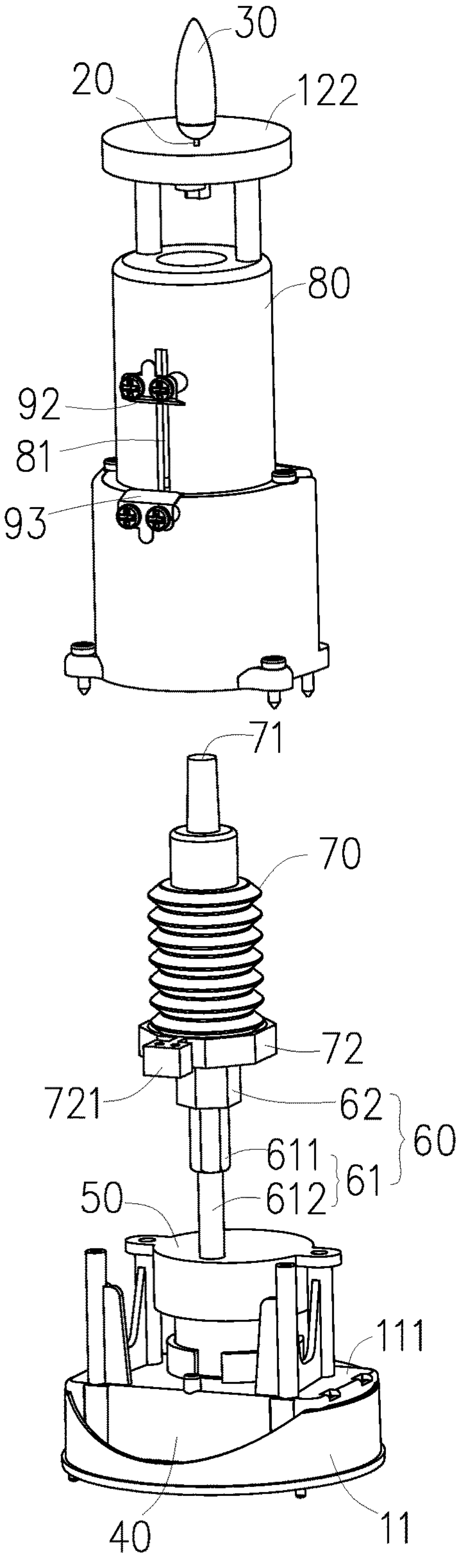
FIG. 3 is an exploded view of a part of the electronic candle in accordance with an embodiment of the present invention.

As shown in FIGS. 1 to 3, in an embodiment of the present invention, an electronic candle mainly includes a housing 10, an electric wire 20 extending from an upper end of the housing 10, a flame piece 30 connected to a tail end of the electric wire 20, a control circuit 40 arranged in the housing 10 and electrically connected to the other end of the electric wire 20, a driving device 50 electrically connected to the control circuit 40, and an actuating device 60 driven by the driving device 50, a container 70 for containing liquid, and an inner cover 80.

The housing 10 is substantially cylindrical and includes a base 11 and an upper cover 12 buckled on the base. The upper cover 12 is used for simulating a candle body of a candle, and may be made of paraffin wax in order to improve the simulation effect. The base 11 may be made of an electrically insulating material, such as plastic. An opening 121 is defined in the middle of the upper end of the upper cover 12 and is sealed by an electrically insulating tray 122.

Figure 4:
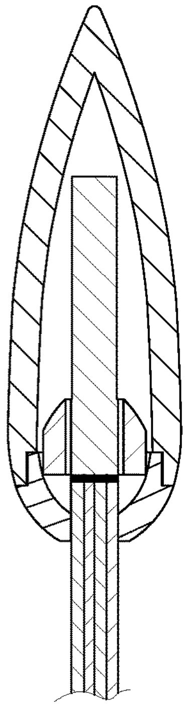
FIG. 4 is a schematic cross-sectional view of a flame piece of an electronic candle in accordance with an embodiment of the present invention.

The tray 122 is preferably made of an environmentally friendly, non-toxic plastic or other polymeric material that is colored to conform to the upper cover 12. The tray 122 has a concave shape for simulating a concave portion formed by melting a top portion of the candle body after a real candle is burned. Two holes 1221, 1222 are formed in the tray 122, wherein the hole 1221 is located at the center of the tray and used as a wire hole, the electric wire 20 passes through the hole 1221, and a gap between the electric wire and the hole 1221 is sealed and waterproof. The electric wire 20 and its portion extending out of the housing 10 should be encased in a black hard outer skin to simulate color and state of a candle wick. A flame piece 30 is fixed to the tail end of the electric wire 20 for imitating a flame of a burning candle. The structure of the flame piece 30 is shown in FIG. 4, and has been disclosed by the Chinese utility model patent ZL 201620728691.1 (issued on Jan. 18, 2017), the U.S. utility patent U.S. Ser. No. 10/436,396 (issued on Oct. 8, 2019) and the German utility model patent DE 202017103857.2 (issued on Sep. 14, 2017).

The hole 1222 is located adjacent the hole 1221. The container 70 is fixed below the hole 1221, and an opening 71 of the container 70 is hermetically connected to an inner surface of the tray 122 of the housing 10, such that the hole 1222 communicates only with the inner space of the container 70. The liquid inside the container 70 can only flow out and in through the hole 1222. In the present embodiment, the container 70 is a stretchable container which can be stretched and shrank in a height direction of the electronic candle, a tube extending from an upper end of the container 70 toward the upper end of the housing, and the opening 71 is defined in a top end of the tube. The top end of the tube is hermetically connected to the inner surface of the tray 122. The container 70 is preferably made of an environmentally friendly, non-toxic material, such as a polypropylene material, for containing an aromatic liquid.

The driving device 50 is used to drive the actuating device 60 to perform a squeezing action and a loosening action on the container 70 to squeeze liquid from the container 70 onto the tray 122 or to draw liquid from the tray 122 back into the container 70.

In this embodiment, the driving device 50 is a micro direct current motor fixed on the base 11 of the housing 10. In order to power the motor, the base 11 is provided with a battery holder 111 with an opening facing outwards, i.e. towards the underside of the electronic candle. The control circuit 40 is fixed to the outer side wall of the battery holder 111, and the driving device 50 and the inner cover 80 are fixed to the side of the bottom of the battery holder facing the upper cover 12. The drive shaft of the driving device 50 extends toward the upper end of the upper cover.

The actuating device 60 includes a lead screw 61 connected to the drive shaft of the driving device 50 and a nut seat 62 connected to a nut 611 of the lead screw 61. The lead screw 61 is parallel to the axis of the electronic candle, the nut 611 is a cylindrical nut, and the nut seat 62 is fixed to one end of the cylindrical nut. When the motor of the driving device 50 rotates in a first direction or a second direction opposite to the first direction, the body 612, with screw threads, of the lead screw 61 rotates therewith, driving the nut 611 to move up or down along the body 612, thereby further driving the nut seat 62 to move up or down. In the present embodiment, when the electronic candle is normally vertically placed, in the set initial state, the nut seat 62 is located at the lowest position, which is located directly below the container 70 and comes into contact with (abuts against) the bottom of the container 70. As the nut seat 62 moves upward, the container 70 performs a squeezing action. When the motor reverses rotation to drive the nut seat 62 to move downward after the squeezing action is performed, the container is relaxed, and the inner space of the container becomes larger. The cylindrical nut 611 allows the end portion of the body 612 of the lead screw 61 not to protrude from the top end portion of the cylindrical nut 611 during operation of the motor. In this embodiment, the nut seat 62 is a hexagonal nut fixed to the upper end of the cylindrical nut 611, and the end thereof serves as a support surface for the container 70.

A position-limit device 90 is provided to prevent the actuating device 60 from over-squeezing or loosening the container 70. That is, the position-limit device 90 serves to limit the maximum (highest) and minimum (lowest) actuation positions of the actuating device 60. In the embodiment, the position-limit device 90 includes a first conductive sheet 91 synchronously moving with the nut seat 62, a second conductive sheet 92 arranged at the maximum actuation position and a third conductive sheet 93 arranged at the minimum actuation position. The first to third conductive sheets 91, 92, 93 are electrically connected to the control circuit 40. When the first conductive sheet 91 and the second conductive sheet 92 are in electrical contact, the motor stops driving the nut seat 62 upward, and when the first conductive sheet 91 and the third conductive sheet 93 are in electrical contact, the motor stops driving the nut seat 62 downward.

In order to fix the position-limit device 90, a fixing ring 72 is sleeved on the outer periphery of the bottom of the container 70, and a protruding portion 721 extending and protruding outwards is formed on the fixing ring 72. The first conductive sheet 91 is fixed to the protruding portion 721. And the first conductive sheet 91 is bent to be generally C-shaped so that the second conductive sheet 92 and the third conductive sheet 93 can be contacted from the upper and lower sides, respectively. The second conductive sheet 92 and the third conductive sheet 93 are both fixed to the outer surface of the inner cover 80. In this embodiment, the inner cover 80 covers the outside of the driving device 50, the actuating device 60 and the container 70, and in order for the protruding portion 721 of the fixing ring 72 to protrude out of the inner cover 80, the inner cover 80 is formed with a gap 81 as a vacancy-avoiding space on the path in which the protruding portion 721 moves. The tray 122 is also fixed to the inner cover 80 by posts to facilitate assembly and fixing.

When the switch of the electronic candle is turned on, the flame piece 30 emits light, the driving device 50 synchronously starts to work, the actuating device 60 is driven to squeeze the container 70, the liquid in the container 70 is slowly squeezed into the concave portion (i.e. the tray 122) of the upper end of the housing 10, and when the liquid level in the concave portion reaches the preset position (i.e. when the first conductive sheet of the actuating device 60 contacts the second conductive sheet); the driving device stops working. When the switch of the electronic candle is turned off, the flame piece 30 is extinguished, the drive motor drives the actuating device to reset until the first conductive sheet contacts the third conductive sheet, the container 70 is slowly released and finally restored to the original state, and the liquid in the concave portion of the upper end of the housing is slowly drawn back into the container. Therefore, the phenomenon that molten wax water is formed at the upper end of the candle body when the candle burns, and the candle water solidifies and seems to disappear after the candle is extinguished is vividly simulated. In addition, when the liquid is a fragrant liquid, it can send out fragrance on the tray to achieve the effect of aromatherapy. When not in use, the liquid is drawn back, which can be used for a long time, with less consumable materials and low use cost. Replacing and replenishing the fragrance liquid is convenient and easy to operate. By controlling the working speed of the driving device, adjusting the speed of liquid outlet and the speed of liquid withdrawal, the simulation effect is better.

In addition, the control circuit may further include a remote-control signal receiving device so that the electronic candle may be remotely controlled using the remote control. When multiple simulation candles are simultaneously used, a single remote controller may control multiple candles at the same time, and the use is more convenient. The remote-control signal receiving device may be an infrared signal receiving device or a wireless radio frequency signal receiving device.

In the embodiments described above, only a single switch may be used to simultaneously control the flame piece and the driving device. It will be understandably that in other embodiments, multiple switches may be used to separately control the flame piece and the driving device.

In addition, in alternate embodiments, the driving device and actuating device may be omitted. If the phenomenon of wax water generated when the candle is burnt is simulated, water can be directly poured at the concave portion of the upper end of the housing. The inner container can be used for storing concentrated aromatic liquid, and the purpose of aromatherapy is realized by adding water directly from the top to dilute and release the aromatic liquid when being used. After being used for a period of time, when the aromatic liquid in the concave portion volatilizes, it can be used by adding water directly. When the concentration of the aromatic liquid decreases and the effect is not good, the aromatic liquid can be saved by further adding high concentration aromatic liquid.

It is understandably that in other alternative embodiments, the driving device may be eliminated, and a knob may be provided in a lower portion of the base of the housing, the other end of which is connected to a screw end of the lead screw. When the knob is rotated in the positive direction or the reverse direction, the lead screw is driven to rotate, the nut seat is moved upwards or downwards, the container is squeezed and loosened, and the function that liquid in the container flows into the tray or is sucked back into the container is achieved.

In the embodiment, since the candle body is thick, only the tray 122 is concave, and it is understandably that in other embodiments, when the candle body is thin, the upper end of the upper cover 12 may be integrally concave after the tray 122 is assembled. Or the upper end of the upper cover is formed by a tray.

In the embodiment, the container is a collapsible container that can be extended and retracted in the direction of the height of the electronic candle, and it is understandably that in other embodiments, the container may be made of a soft, flexible material. As long as the container is deformable when the actuating device moves upwards, the liquid in the container can be squeezed out. In other embodiments, the tube of the container may be omitted.

In other embodiments, the inner cover may be replaced by a support frame made of plates or/and posts so long as the actuating device, the position-limit device, and the tray are fixed in predetermined positions. It is understandably that the inner cover or support bracket may also be eliminated and the actuating device and the position-limit device may be fixed to an inner wall of the upper cover.

In other embodiments, a generally C-shaped fixing claw may be used in place of the fixing ring to clamp the bottom of the container.

In other embodiments, the fixing ring may be fixedly connected to the nut seat and is integrally cup-shaped as part of the nut seat to support the bottom of the container. That is, a fixing ring or a fixing claw surrounding the bottom of the container is arranged on the nut seat, a protruding portion extending outwards is formed on the fixing ring or the fixing claw, and the first conductive sheet is fixed on the protruding portion, and the same function can be realized.

It is understandably that in other embodiments, the driving device may include an air cylinder. The actuating device may include a support block connected to the tail end of the cylinder rod in place of a nut seat. During operation, the air cylinder pushes the air cylinder rod to move upwards to drive the support block to extrude the container upwards. As the cylinder rod retracts, the support block moves downward, releasing the container. In order to prevent liquid splashing, buffer unit, such as springs or shrapnel, may be provided between the cylinder rod and the support block so that the support block moves relatively gently during operation.

It is understandably that in other embodiments, more complex mechanical mechanisms may be used to replace the actuating devices of the previous embodiments for the purpose of squeezing and releasing the container.

It is understandably that in other embodiments, other position sensing devices, such as photoelectric sensor, may be used in place of the position-limit device to achieve a fixed movement path for the actuating device.

In describing the present invention, it is to be understood that terms indicating orientation or positional relationship, such as “upper”, “lower”, “vertical”, “horizontal”, “top”, “bottom”, “inner”, “outer”, is based on the orientation or positional relationship shown in the drawings for the purpose of describing the invention and simplifying the description only, and is not intended to indicate or imply that the referenced device or element must have a particular orientation, be constructed and operated in a particular orientation, and therefore should not be construed as limiting the invention.

While the invention has been described in terms of several exemplary embodiments, those skilled on the art will recognize that the invention can be practiced with modification within the spirit and scope of the appended claims. In addition, it is noted that, the Applicant’s intent is to encompass equivalents of all claim elements, even if amended later during prosecution.

What is claimed is:

1. An electronic candle, comprising:

a housing having a concave portion at its upper end, the concave portion defining a wire hole and a through hole;

a container configured for containing liquid and arranged in the housing;

a flame piece configured above the housing; and a control circuit arranged in the housing and electrically connected with the flame piece via an electric wire passing through the wire hole;

wherein an opening of the container is hermetically connected with the upper end of the housing, and the through hole communicates with an inside of the container via the opening.

2. The electronic candle according to 1, further comprising:

a driving device electrically connected with the control circuit; and an actuating device driven by the driving device;

wherein the actuating device is configured to perform squeezing and loosening actions on the container under the driving of the driving device.

3. The electronic candle according to 2, wherein the driving device comprises a motor, the actuating device comprises a lead screw connected to an output shaft of the motor and a nut seat connected to a nut of the lead screw, and when the electronic candle is normally vertically placed, the nut seat is positioned right below the container; when the motor rotates, the nut of the lead screw is driven to move up and down on the body of the lead screw, and then the nut seat is driven to perform squeezing and loosening actions on the container.

4. The electronic candle according to 3, further comprising a position-limit device for limiting a maximum actuation position and a minimum actuation position of the actuating meaning.

5. The electronic candle according to 4, wherein the position-limit device comprises:

a first conductive sheet synchronously moving with the nut seat;

a second conductive sheet arranged at the maximum actuation position; and a third conductive sheet arranged at the minimum actuation position;

wherein the first conductive sheet to the third conductive sheet are electrically connected with the control circuit, respectively.

6. The electronic candle according to 5, wherein a fixing ring is sleeved on a bottom of the container or a fixing claw is clamped on the bottom of the container, a protruding portion extending outwards is formed on the fixing ring or the fixing claw, and the first conductive sheet is fixed on the protruding portion.

7. The electronic candle according to 6, further comprising an inner cover or a support frame arranged on outer sides of the driving device, the actuating device and the container, a gap for the protruding portion to extend is defined in the inner cover or the support frame, and the second conductive sheet and the third conductive sheet are fixed on the inner cover or the support frame.

8. The electronic candle according to 5, wherein a fixing ring or a fixing claw surrounding a bottom of the container is arranged on the nut seat, a protruding portion extending outwards is formed on the fixing ring or the fixing claw, and the first conductive sheet is fixed on the protruding portion.

9. The electronic candle according to 8, further comprising an inner cover or a support frame arranged on the outer sides of the driving device, the actuating device and the container, a gap for the protruding portion to extend is defined in the inner cover or the support frame, and the second conductive sheet and the third conductive sheet are fixed on the inner cover or the support frame.

10. The electronic candle according to 1, wherein the control circuit comprises a remote-control signal receiving device.

* * * * *